(12) United States Patent
Johnson et al.

(10) Patent No.: US 6,642,426 B1
(45) Date of Patent: Nov. 4, 2003

(54) FLUID-BED AROMATICS ALKYLATION WITH STAGED INJECTION OF ALKYLATING AGENTS

(76) Inventors: David L. Johnson, 181 Concord Meeting Rd., Glenn Mills, PA (US) 19342; Robert G. Tinger, 8 Valerie Ct., Malaga, NJ (US) 08328; Robert A. Ware, 8055 Stenton Ave., Wyndmoor, PA (US) 19038; Sergei Yurchak, 211 Timber Jump La., Media, PA (US) 19063

( * ) Notice: Subject to any disclaimer, the term of this patent is extended or adjusted under 35 U.S.C. 154(b) by 0 days.

(21) Appl. No.: 09/166,188

(22) Filed: Oct. 5, 1998

(51) Int. Cl.[7] .......................... C07C 15/067; C07C 2/64
(52) U.S. Cl. .................. 585/449; 585/446; 585/467
(58) Field of Search .................. 585/446, 449, 585/467

(56) References Cited

U.S. PATENT DOCUMENTS

| | | | | |
|---|---|---|---|---|
| 3,751,504 A | | 8/1973 | Keon et al. ............... 260/672 T |
| 4,100,217 A | * | 7/1978 | Young .................... 260/671 R |
| 4,377,718 A | | 3/1983 | Sato et al. .................. 585/467 |
| 4,761,513 A | | 8/1988 | Steacy ........................ 585/467 |
| 4,992,607 A | * | 2/1991 | Harandi et al. ............. 585/467 |
| 5,120,890 A | | 6/1992 | Sachtler et al. ............. 585/449 |
| 5,198,595 A | * | 3/1993 | Lee et al. ................... 585/467 |
| 5,600,048 A | * | 2/1997 | Cheng et al. ............... 585/449 |

* cited by examiner

Primary Examiner—Thuan D. Dang

(57) ABSTRACT

A system and process for producing xylene and other alkylated aromatics includes one or more fluidized bed reaction zones that provide contact between the reactants (i.e., an aromatic reactant and an alkylating reagent). Improved conversion and selectivity is realized when the alkylating reagent is stagewise injected into the fluidized bed at one or more locations downstream from the location of aromatic reactant introduction into the fluidized bed. Preferably, the alkylating reagent is introduced at a plurality of locations along the axial direction of the fluidized bed reaction zone, or at plural locations between a plurality of different fluidized bed reaction zones.

17 Claims, 2 Drawing Sheets

FLUID-BED AROMATICS ALKYLATION WITH STAGED INJECTION OF ALKYLATING AGENTS

BACKGROUND OF THE INVENTION

A. Field of the Invention

This invention relates to an improved system and process for alkylating aromatics using a fluidized bed reactor. The improved results of this invention are realized by injecting at least a portion of the alkylating reagent downstream from the location where the aromatic reactant is introduced. This can be accomplished, for example, by directly introducing the alkylating reagent into the fluidized bed, preferably at plural stages along the flow axis of the reactor. Alternatively, the alkylating reagent can be injected into a region between two separate and discrete fluidized beds. Preferably, a portion of the alkylating reagent also is introduced along with the aromatic reactant, or at least near the location where the aromatic reactant is introduced.

The processes and systems according to the invention can be used for any suitable aromatic alkylation reaction. This invention is particularly well suited for use in a process for producing xylene (preferably para-xylene) from toluene and methanol. When the invention is used in this procedure, a significant improvement in toluene conversion, methanol selectivity, and selectivity to para-xylene can be realized. The invention also can be used, for example, in the production of other alkylaromatics including, for example, ethylbenzene, cumene, diethylbenzene, diisopropylbenzene, para-ethyltoluene, para-cymene, and pseudocumene, and for the reduction of benzene in motor fuels.

B. Description of the Prior Art

Aromatic alkylation is an important procedure for producing many useful chemical products. For example, para-xylene, which can be produced by alkylating toluene with methanol, constitutes an important starting material for manufacturing terephthalic acid, which is an important intermediate in production of synthetic polyester fibers, films, or resins. These polyester materials have many practical, well known uses, such as in fabrics, carpets, and apparel. Ethylbenzene, which can be produced by alkylating benzene with ethylene, is used mainly as a precursor for styrene production. Styrenes and polystyrenes are well known for many uses and products, including: packaging and disposable serviceware associated with the food industry; audio and visual cassettes; medical and dental molding products; and synthetic plastics, rubbers, and foams.

Because of the importance of alkylated aromatic products as starting materials and intermediates for producing many common consumer and industrial products, efficient production and use of alkylated aromatics is of great importance. Additionally, most aromatic starting materials, such as toluene and benzene, are obtained during oil and gas production. Therefore, efficient alkylation of these aromatic materials is vital to eliminate wastes and conserve precious natural resources.

A conventional approach for toluene alkylation includes mixing toluene and methanol upstream of a reactor and then feeding the mixture together into the base of the reactor. The reactor includes an alkylation catalyst in one or more fixed beds, and this catalyst promotes the alkylation reaction between the toluene and methanol to produce xylene. While this approach has been used successfully, its yield and reactant utilization characteristics leave room for improvement.

In an effort to improve yields in various reaction procedures, stagewise injection of reagents has been used in various fixed bed processes. For example, U.S. Pat. Nos. 4,377,718 and 4,761,513 describe toluene alkylation processes wherein the alkylating reagent is fed at different stages between fixed beds. Likewise, U.S. Pat. No. 3,751,504 discloses a similar procedure, using multiple injection ports, for preparing ethylbenzene using a fixed bed catalyst reactor. U.S. Pat. No. 5,120,890 discloses multiple reactant injection locations into separate fixed beds in a process for reducing benzene and toluene content in light gasoline streams. U.S. Pat. Nos. 3,751,504; 4,377,718; 4,761,513; and 5,120,890 are each entirely incorporated herein by reference.

In these fixed bed processes, one can easily separate the catalyst load into several different and discrete zones. During use, product from one zone is mixed with additional alkylating reagent, and this mixture is fed to the subsequent zone. One way of providing these separate and discrete zones includes placing each zone in a separate reactor vessel, wherein additional reagent(s) is (are) injected between adjacent zones. This procedure suffers from the drawback that considerable expense is involved in providing separate reactor vessels and the associated hardware for running this type of system.

Additionally, fixed bed reactors are disadvantageous for exothermic reactions because of the potential negative impact of exotherms on product selectivity. Reactor stability concerns with fixed beds also require that the temperature rise per catalyst bed be limited. This could necessitate a large number of beds to accommodate the heat of reaction. Similarly, endothermic reactions would result in reduced reaction rates and excessive catalyst requirements.

SUMMARY OF THE INVENTION

It is an object of this invention to provide processes and systems for alkylating aromatic reactants with high conversion and selectivity, e.g., for producing para-xylene from an alkylating reaction between toluene and methanol: In general, the processes and systems according to this invention use stagewise injection of the alkylating reagent (e.g., methanol) at a location downstream from the location where the aromatic reactant is initially introduced into the fluidized bed.

A first aspect of this invention relates to a process for alkylating an aromatic reactant (e.g., methylating toluene to xylene). The process includes introducing the aromatic reactant (e.g., toluene) into a fluidized bed reaction zone, wherein the fluidized bed reaction zone includes a top portion, a bottom portion, and an intermediate portion extending between the top portion and the bottom portion. The alkylating reagent (e.g., methanol) is introduced directly into the intermediate portion of the fluidized bed reaction zone, where it reacts with the aromatic reactant (e.g., toluene) to produce the alkylated aromatic product (e.g., xylene). This product is recovered from the fluidized bed reaction zone.

In addition to introducing alkylating reagent directly into the intermediate portion of the fluidized bed reaction zone, alkylating reagent also may be introduced into the bottom portion of the fluidized bed reaction zone. This additional alkylating reagent can be introduced in a common feed stream with the aromatic reactant, or it can be separately fed into the fluidized bed reaction zone.

One preferred embodiment of the process according to the invention includes. introducing alkylating reagent directly into the intermediate portion of the fluidized bed reaction zone at a plurality of locations. These plural locations preferably are provided at a plurality of different axial positions in the intermediate portion of the fluidized bed reaction zone. Also, the alkylating reagent can be introduced at a plurality of different locations in the plane perpendicular or substantially perpendicular to the axial direction of the reactor vessel (i.e., at plural locations at each stage of its introduction).

Another embodiment of the process according to the invention includes the use of two or more fluidized bed reaction zones arranged in series. Preferably, the aromatic reactant is introduced into a first fluidized bed reaction zone of the series, i.e., the zone located furthest upstream. The alkylating reagent may be introduced into a region of the reactor system between the first fluidized bed reaction zone and a second fluidized bed reaction zone. During operation, the aromatic and alkylating reagents react to produce the alkylated aromatic product, which then is recovered from the reactor system.

In this embodiment of the process according to the invention, the first and second fluidized bed reaction zones (or more) can be contained either in a single reactor vessel or in a plurality of reactor vessels arranged in series with respect to the aromatic reactant flow. Preferably, in this embodiment, the alkylating reagent is introduced into the reactor system at a bottom of the second fluidized bed reaction zone (e.g., at the bottom of the second reactor), and, if more than two fluidized bed reaction zones are provided, preferably the alkylating reagent is introduced between each adjacent pair of the reaction zones. As with the first embodiment, if desired, additional alkylating reagent can be introduced into the bottom portion of the first fluidized bed reaction zone, optionally in a common feed stream with the aromatic reactant.

The invention also relates to systems for alkylating an aromatic reactant to an alkylated aromatic product. In this aspect of the invention, a reactor system provides at least a first reactor vessel that contains at least a first fluidized bed reaction zone. An appropriate means is provided for introducing the aromatic reactant into the reactor system at a first location in the first reactor vessel, preferably at the bottom of the most upstream fluidized bed reaction zone A means also is provided for introducing the alkylating reagent into the reactor system at a location downstream from the first location where the aromatic reactant is introduced. At least a portion of the alkylating reagent is introduced within the first fluidized bed reaction zone or at a location between the first fluidized bed reaction zone and a second fluidized bed reaction zone. The system also provides appropriate means for recovering the alkylated aromatic product.

In one preferred embodiment of the system according to the invention, the means for introducing alkylating reagent introduces this reagent at a plurality of locations spaced apart along an axial direction of the first reactor vessel. This reactor vessel may include one or more individual fluidized bed reaction zones. When plural fluidized bed reaction zones are provided, it is preferred that a means for introducing alkylating reagent provide the reagent between each adjacent pair of fluidized bed reaction zones in the series.

Accordingly, this invention provides processes and systems for producing alkylated aromatics (e.g., xylene) from an aromatic reactant (e.g., toluene) and an alkylating reagent (e.g., methanol), wherein the processes and systems provide high conversion, reactant utilization, and product selectivity, particularly when producing para-xylene from toluene and methanol.

BRIEF DESCRIPTION OF THE DRAWINGS

This invention, and the advantageous features thereof, will be more completely understood when considered in context with the following detailed description, which includes a description of the attached drawings, wherein.

DETAILED DESCRIPTION OF THE INVENTION

Figure 2:
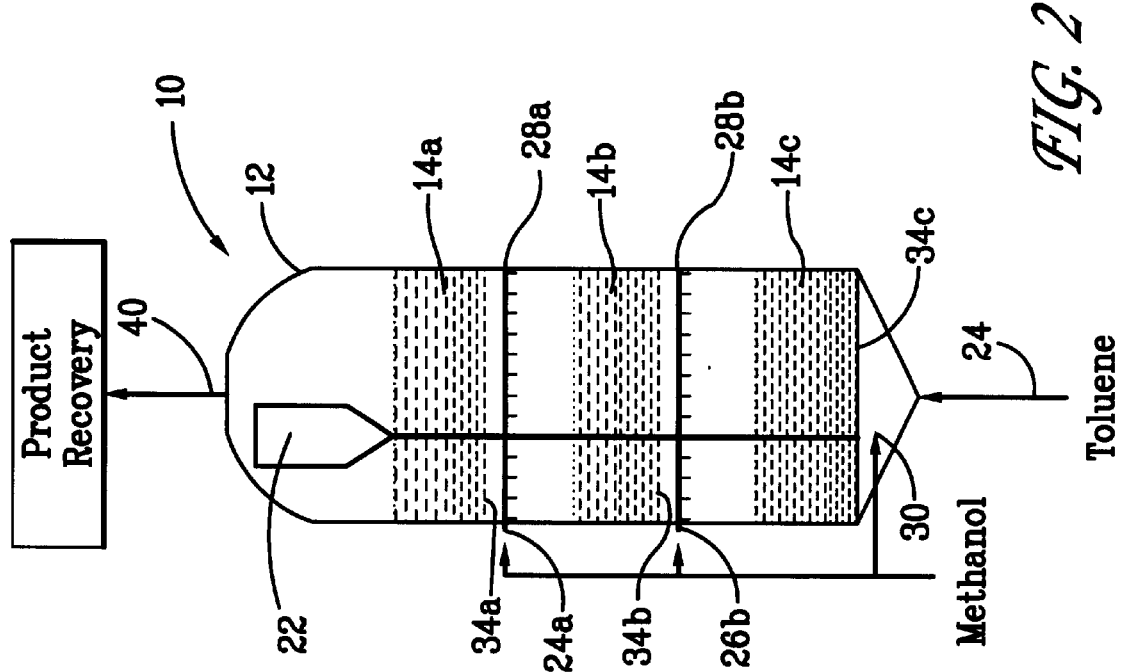
FIG. 2 illustrates an embodiment of the invention that uses a single reactor vessel that includes a plurality of independent and discrete fluidized beds.

During aromatic alkylation reactions, such as methylation of toluene, an aromatic reactant reacts with an alkylating reagent to form the desired alkylated aromatic product. In toluene methylation, the following desired reaction takes place:

Many competing side reactions, however, also can occur. For example, methanol can react with itself, e.g., to form olefins. Because the cost of methanol is a significant part of the cost involved in xylene production, it is important to minimize or eliminate these undesired side reactions. Other undesirable side reactions that can occur during methylation of toluene involve over-alkylation of toluene to form $C_9+$ aromatics.

Such undesired side reactions during toluene methylation can be reduced by using a large excess of toluene during the reaction process. Using excess toluene increases the chances that one methanol molecule will react with one toluene molecule to produce xylene, and it reduces the chances that two or more methanol molecules will react with the same toluene molecule or with themselves. Therefore, using excess toluene results in efficient use of methanol during the reaction by increasing the "methanol utilization" during performance of the reaction. "Methanol utilization," which provides a measure of methanol selectivity to producing xylene, is defined as:

$$\frac{\text{the number of moles of xylene produced} \times 100}{\text{the number of moles of methanol consumed}} = \% \text{ methanol utilization}$$

A xylene production procedure that provides high toluene conversion and high methanol utilization produces xylene in an efficient, desirable manner. Preferably, the product xylenes are rich in the para-isomer and exhibit high para-xylene selectivity, defined as:

$$\frac{\text{Mass para-xylene} \times 100}{\text{Mass ortho-xylene} + \text{Mass para-xylene} + \text{Mass meta-xylene}} = \% \text{ Para-xylene Selectivity}$$

This invention relates to novel reactor systems and processes for improving the conversion, alkylation reagent utilization, and selectivity during alkylation of aromatics in a fluidized bed reactor, e.g., during toluene alkylation to produce xylene. The systems and processes according to the invention provide these improved results by introducing the alkylating reagent (e.g., methanol) into the reactor system at one or more locations downstream in the reactor system from the location where the aromatic reactant (e.g., toluene) is introduced, i.e., in a "stagewise manner." Any number of downstream "stages" can be used for introducing the alkylating reagent, e.g., two to four downstream stages.

Stagewise injection of the alkylating reagent can occur in at least two different manners in the processes according to the invention. First, in a preferred aspect of this invention, the alkylating reagent can be directly injected into an intermediate portion of the fluidized bed itself As an alternative, it can be injected into a region between fluidized beds, if discrete, plural fluidized beds are used for practicing the invention. Each of these systems will be described in more detail below.

As noted above, in a preferred embodiment of the invention, the alkylating reagent is injected directly into the fluidized catalyst bed at a location- downstream from the location where the aromatic reactant is introduced. This alkylating reagent preferably is introduced directly into the catalyst bed without pre-mixing it with the upstream vapors including the aromatic reactant. Given the potential for methanol self-reactions during toluene methylation, as described above, it is surprising that this direct introduction of methanol functions properly in the process of the invention without adversely affecting methanol utilization and xylene yield, This is particularly surprising in the process according to the invention, because the fluidized beds used are relatively dense, such as turbulent sub-transport fluid beds with an operating bed density of about 100 to 600 kg/m$^3$, preferably bout 300to 500 kg/m$^3$, and the use of these dense beds increases the catalyst concentration and the methanol concentration at the area of methanol injection. As will be demonstrated below, however, this direct methanol introduction procedure effectively produces xylene with improved toluene conversion and methanol utilization.

To further reduce the chances of adverse methanol self-reactions, optionally, the alkylating reagent can be pre-mixed with at least a portion of the upstream reactor vapors and/or fresh aromatic feed, outside the presence of the catalyst. This mixture then is introduced into the fluidized bed at a location in the intermediate portion of the fluidized bed, which contains the alkylation catalyst. The upstream reactor vapors may contain unreacted aromatic and alkylating reagents and some alkylated aromatic product. While this option reduces the chances of adverse methanol/methanol side reactions, it increases expenses and reactor complexity.

In an alternative embodiment of the invention, as mentioned above, the reactor system contains plural, discrete fluidized beds. The downstream, stagewise injected alkylating reagent in this embodiment can be introduced into the reactor system either directly into one or more of the fluidized beds, as described above, or into a region between two discrete fluidized beds. While this embodiment effectively produces alkylated aromatic products in high yield with high conversion and high alkylating reagent utilization, significant additional expenses are involved in maintaining the discrete fluidized beds. If discrete fluidized beds are to be maintained, a means must be provided to separate the catalyst from the vapor in each zone and to maintain the proper inventory of catalyst and reactants in each zone. The simplest way to do so involves placing each fluidized bed in a separate reactor vessel. If a single reactor vessel contains two or more fluidized beds, means must be provided (such as a perforated grid plate) to support and control the level of each fluidized bed and to return catalyst particles entrained in the gas flow to the fluidized bed (i.e., to prevent catalyst entrained in the gas flow from migrating between beds).

Specific embodiments of the invention will now be described in greater detail. Throughout this application, the invention often is described in terms of its preferred embodiments. Indeed, one of the preferred aspects of this invention relates to improved systems and processes for producing para-xylene from reaction of toluene and methanol, wherein the resulting systems and processes produce para-xylene in a highly selective manner, with improved toluene conversion and improved methanol utilization. Those skilled in the art will recognize, however, that the use of this invention for producing xylene from toluene and methanol is merely one example of the usefulness of the invention. The invention can be used for any other suitable reaction process, such as alkylation of other aromatics (e.g., ethylation of benzene to produce ethylbenzene, propylation of benzene to produce cumene, ethylation of ethylbenzene to produce diethylbenzene, propylation of cumene to produce diisopropylbenzene, ethylation of toluene to produce para-ethyltoluene, propylation of toluene to produce para-cymene, and methylation of xylene to produce pseudocumene [1,2,4-trimethyl benzene]) and reduction of benzene content in motor fuels.

Figure 1:
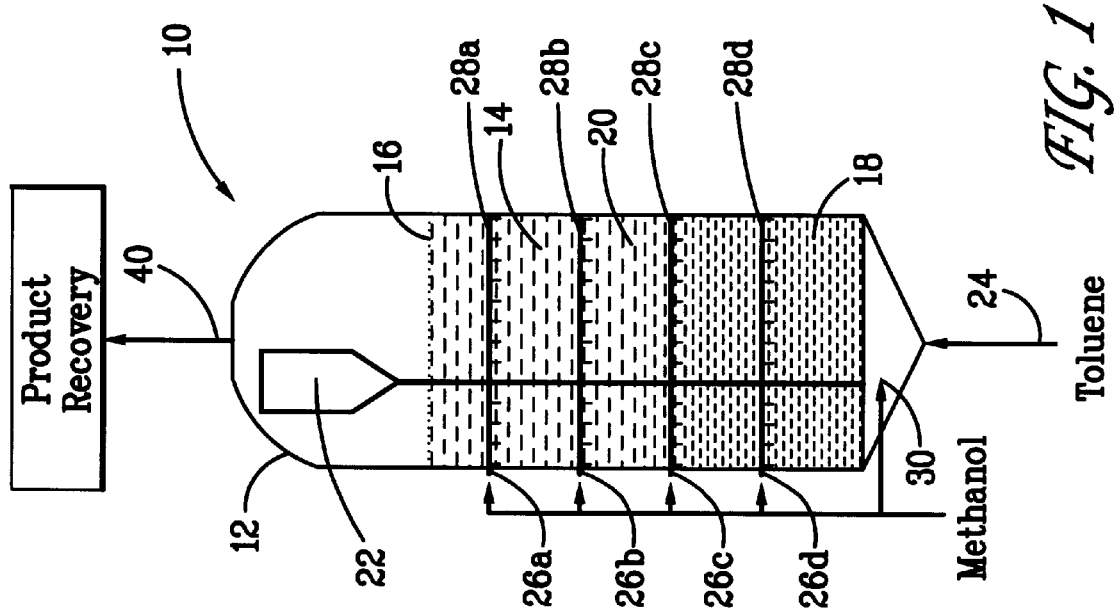
FIG. 1 illustrates an embodiment of the invention that uses a single reactor vessel that includes a single fluidized bed.
Figure 3:
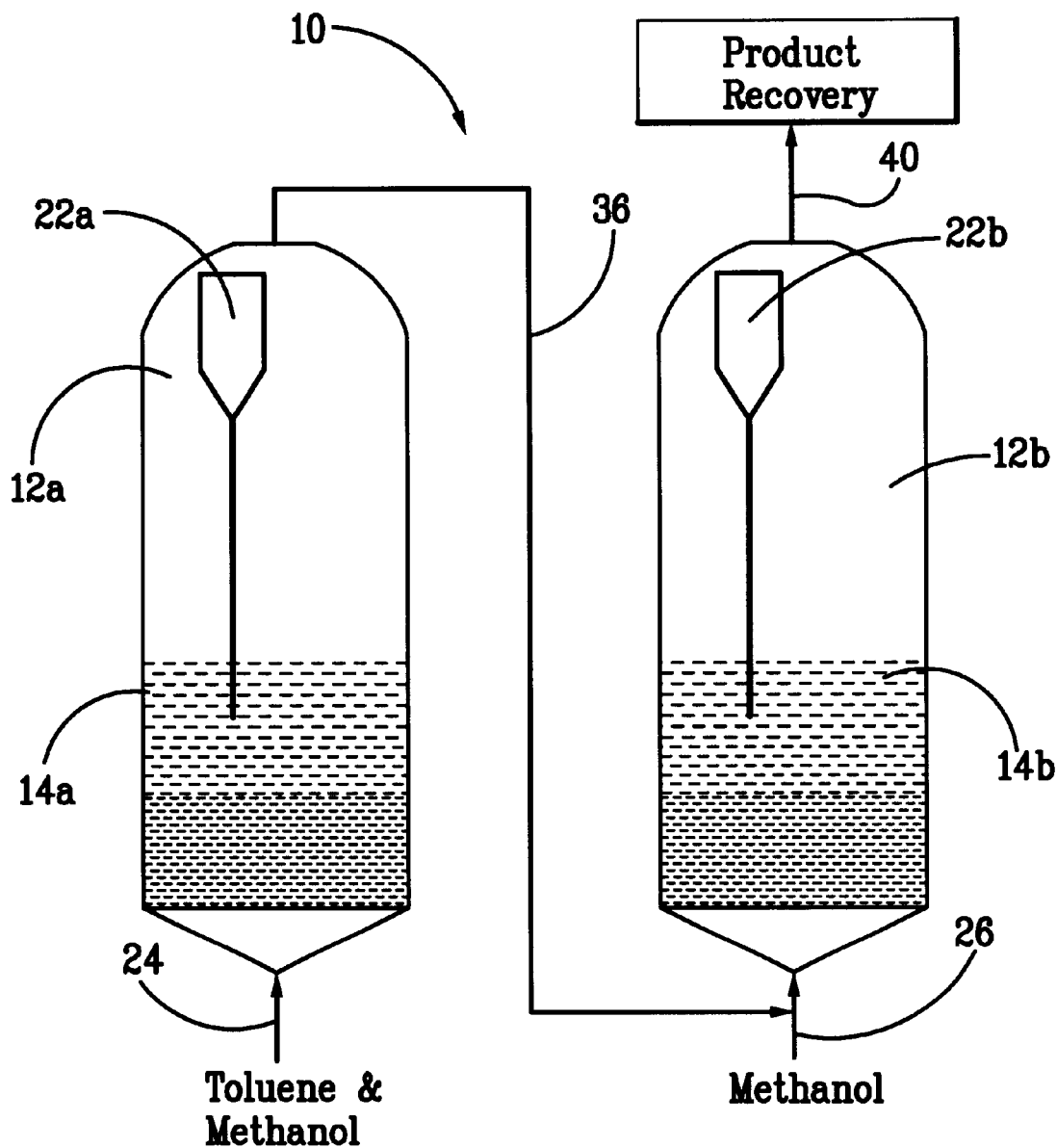
FIG. 3 illustrates an embodiment of the invention that uses plural reactor vessels, each including a fluidized bed.

FIGS. 1–3 schematically illustrate various different fluidized bed reactor systems that can be used in this invention for alkylating aromatic reactants. The illustrated systems are described in detail below, wherein the same reference number is used throughout the figures to designate the same part.

FIG. 1 illustrates a relatively compact and simple embodiment of the system 10 according to the invention. The system 10 includes a reactor vessel 12, which contains a single fluidized bed reaction zone 14. This reaction zone 14 includes a top portion 16, a bottom portion 18, and an intermediate portion 20 that extends between the top portion 16 and the bottom portion 18.

A fluidized bed reaction zone 14, as is known in the art, contains a volume of small sized particles that are generally kept afloat ("fluidized") by flowing gas as it passes upward through the reactor vessel 12 during reactor operation. Conventional devices, such as cyclone 22, can be used to provide primary separation and recovery of entrained catalyst from the gas, to return the solids to the bed, to recover some or all of the gas necessary to mix and contact the various reactants and catalyst, and to maintain the fluidized bed 14 under suitable operating conditions. Through this gas flow, reactants pass into and/or through the reaction zone 14, and the small particles provide a large surface area that allows generous contact between the reactants under the alkylation conditions.

Preferably, the fluidized bed 14 will contain a catalyst that promotes the alkylation reaction, and indeed, if desired, the entire volume of the fluidized bed 14 may constitute catalyst particles. Any suitable alkylation catalyst can be used without departing from the invention. For example, the ZSM-5 zeolite alkylation catalyst described in WO 98/14415 is suitable for use in the processes and systems of this invention. The disclosure of WO 98/14415 is entirely incorporated herein by reference. Selectivated catalysts (i.e., catalysts treated to preferentially produce a particular isomer of a compound, such as para-xylene) can be used in the process of the invention. Such selectivated catalysts are known in this art.

For the reaction to proceed, the various reactants must be introduced into the fluidized bed reaction zone 14. Although the specific location is not critical to the process and system according to the invention, in the illustrated embodiment the aromatic reactant (e.g., toluene in this system) is introduced at the bottom portion 18 of the fluidized bed reaction zone 14. This reactant can be introduced using any appropriate introduction device 24, including conventional devices known in the art (e.g., injector nozzles, perforated grids, pipe grids, etc.). The aromatic reactant can be introduced at one or more locations in the fluidized bed reaction zone 14, but preferably these locations are provided at or near its bottom portion 18. The aromatic reactant preferably is introduced in gaseous form and provides at least a portion of the gas flow necessary for maintaining the reaction zone 14 in fluidized form.

In accordance with the invention, the alkylating reagent (e.g., methanol in this system) can be introduced directly into the fluidized bed reaction zone 14 at one or more locations along its axial direction, downstream from the location where the aromatic reactant is introduced (via introduction device 24). The illustrated reactor system includes four downstream axial introduction devices 26a, 26b, 26c, and 26d for introducing the alkylating reagent in different "stages." These devices 26a, 26b, 26c, and 26d may be arranged to introduce the alkylating reagent in any appropriate manner. For example, each device 26a, 26b, 26c, and 26d may include one, and preferably more, injector nozzles located around the periphery of the reactor vessel 12 for introducing the alkylating reagent around the vessel periphery. As another alternative, each device 26a; 26b, 26c, and 26d may include a manifold or pipe grid arrangement 28a, 28b, 28c, and 28d, as shown in FIG. 1, for introducing the alkylating reagent at a plurality of locations in the interior of the fluidized bed reaction zone 14. Preferably, each axial stage includes suitable devices for introducing the alkylating reagent at plural locations within the stage. This stagewise introduction of methanol at various multiple locations increases methanol utilization, the toluene conversion percentage, and the selectivity to the desired xylene product.

Also, if desired, another alkylating reagent introduction device or port could be provided above the top portion 16 of the fluidized bed, without departing from the invention.

One preferred aspect of the invention includes introducing additional alkylating reagent at or near the location where the initial aromatic reactant is introduced. FIG. 1 shows introduction device 30 at the bottom of the reactor vessel 12 for introducing this additional alkylating reagent. If desired, this additional alkylating reagent and the aromatic reactant can be mixed together prior to introducing the materials into the bottom 18 of the fluidized bed reaction zone 14, such that these materials are introduced in a common feed stream. Alternatively, the materials can be introduced separately into the fluidized bed reaction zone 14 and contacted together after their introduction, or the materials can be first mixed together in a nozzle or other device that introduces both concurrently into the fluidized bed reaction zone 14. Any suitable mixing device and method can be used for this introduction without departing from the invention.

If necessary, the devices 24, 26a, to 26d, 28a to 28d and 30 introducing the various reagents and reactants can be maintained under conditions so as to ensure the integrity of these materials through the mechanical device until the reactants or reagents enter the catalyst bed (i.e., to prevent undesired side reactions, conversions, and/or degradation of the reactants or reagents). This can be accomplished in any suitable manner, such as by limiting residence time of the materials in the introduction device or by cooling the introduction device to a temperature that maintains the reagent or reactant under stable conditions.

The reactor vessel 12 and the reactant introduction rates are maintained under suitable conditions to support a chemical reaction between the aromatic reactant and the alkylating reagent to produce the desired alkylated aromatic product. This reaction product preferably is produced in a gaseous form, and it may be collected and recovered from the reactor outlet stream 40 in any suitable manner, such as by condensation and subsequent fractionation of the hydrocarbon liquid using conventional distillation and recovery equipment. Further purification of the product canoe accomplished in any suitable manner, for example, by crystallization or solid adsorption (e.g., a Parex process).

Unreacted feeds can be recycled to the fluidized bed reaction zone, 14. It is generally not necessary to completely purify the recycled methanol and toluene;, although this can be done, if desired.

Suitable reaction conditions, particularly for methylation of toluene with methanol to produce para-xylene, include the following ranges:

(a) Temperature—about 500° to about 700° C., and preferably between about 500° to about 600° C.;

(b) Pressure—about 1 atmosphere to about 1000 psig (about 100 to about 7000 kPa), and preferably about 10 psig to about 200 psig;

(c) moles toluene/moles methanol (in the reactor charge)—at least about 0.2, and preferably from about 0.2 to about 20; and (d) a weight hourly space velocity ("WHSV") for total hydrocarbon feed to the reactor(s) of about 0.2 to about 1000, preferably about 0.5 to about 500 for the aromatic reactant, and about 0.01 to about 100 for the combined alkylating reagent stage flows, based on total catalyst in the reactor(s).

The process is preferably conducted in the presence of added hydrogen and/or added water such that the molar ratio of hydrogen and/or water to toluene+methanol in the feed to the reactor is between about 0.01 and about 10. Those skilled in the art will be capable of adjusting the various reaction parameters and conditions to optimize conversion, yield, and selectivity, using routine experimentation.

A second exemplary system 10 for use in this invention is illustrated in FIG. 2. Like the system 10 of FIG. 1, this second system 10 includes a single reaction vessel 12, but this vessel 12 includes plural, discrete fluidized bed reaction zones 14a, 14b, and 14c, arranged in series. Although any appropriate number of fluidized bed reaction zones could be used in a reactor vessel 12 without departing from the invention, the illustrated embodiment of the invention includes three zones 14a, 14b, and 14c. Systems that maintain multiple fluidized beds are described, for example, in D. Kunii and O. Levenspiel, Chapter 2 of *Fluidization Engineering*, Second Edition (1991), Butterworth-Heinemann, Boston, which book is entirely incorporated herein by reference.

Each fluidized bed reaction zone 14a, 14b, and 14c can contain the same fluidized bed materials (e.g., catalyst and other small solid particles), if desired. Preferably, the catalyst and the bed characteristics are selected appropriately so as to optimize the conversion, yield, and selectivity. Additionally, the fluidized bed volume and the content of the reactants in each of the individual fluidized beds may be factors that influence the conversion, yield, and selectivity. Using routine experimentation, the skilled artisan will be able to control and select the various properties of the fluidized beds and the reactor systems to obtain optimal results.

In the system 10 of FIG. 2, the aromatic reactant (e.g., toluene) is introduced into the system into the bottom of the most upstream fluidized bed 14c, through an introduction device 24 like that used in the embodiment of FIG. 1. The alkylating reagent is introduced at one or more locations provided downstream from the introduction device 24, either directly into one or more of the fluidized beds, as shown in FIG. 1, or into an open region between two adjacent fluidized beds, as shown in FIG. 2. While FIG. 2 illustrates alkylating introduction devices 26a and 26b, with manifolds or pipe grids 28a and 28b located between each adjacent pair of fluidized beds, 14a/14b and 14b/14c, only one of these introduction systems could be used without departing from the invention. Additionally, as described above in conjunction with FIG. 1, alkylating reagent can be introduced into the system 10 at a location above the furthest downstream fluidized bed reaction zone 14a. Also, additional alkylating reagent can be introduced at the bottom of the most upstream fluidized bed 14c, through introduction device 30, as described above with respect to FIG. 1.

Like the system illustrated in FIG. 1, a cyclone 22 and/or the aromatic reactant gas inlet flow are used to maintain the fluidized bed reaction zones 14a, 14b, and 14c in a fluidized condition. Screening devices (e.g., perforated grids) are provided to maintain the fluidized beds 14a, 14b, and 14c in their separate and discrete zones. Lower screen grids 34a and 34b maintain the lower boundary of fluidized beds 14a, 14b respectively while inhibiting movement of fluidized bed and catalyst particles between adjacent fluidized beds under the force of gravity. Lower screen grid 34c provides a base for the lowermost fluidized bed 14c. The catalyst inventory of the fluidized beds is maintained by return of solids to the beds from the cyclone recovery system.

The alkylated aromatic product "from the reactor outlet stream 40" in the system according to FIG. 2 is collected from the hydrocarbon liquid after condensation and fractionation, as described above.

A third embodiment of the system 10 according to the invention is illustrated in FIG. 3. Unlike the other illustrated systems, this system 10 includes independent reactor vessels 12a and 12b, arranged in series, each of which contains a single, separate fluidized bed reaction zone 14a and 14b, respectively. In this embodiment, the initial aromatic reactant charge is introduced into the bottom of the upstream fluidized bed 14a in the first reactor vessel 12a through inlet device 24. The aromatic reactant is introduced into the first reactor vessel 12a along with an alkylating reagent charge. While the illustrated embodiment shows these two reactants introduced via the same inlet device 24, they can be introduced separately, as described above.

Some of the aromatic reactant and alkylating reagent react in the upstream fluidized bed reaction zone 14a to produce the alkylated product. Unreacted aromatic reactant and alkylating reagent, along with the reaction products, exit the first fluidized bed 14a and the first reactor vessel 12a via transfer device 36 (e.g., a pipeline or other suitable transfer device), through which they are transferred to the bottom of the second reactor vessel 12b. Here, these reactants from the first vessel 12a are introduced into the fluidized bed 14b of the second reactor vessel 12b. Fresh alkylating reagent also is introduced into the bottom of the second fluidized bed reaction zone 14b, via introduction device 26. Any suitable device 26 or method can be used for introducing the fresh alkylating reagent, such as those described above in FIGS. 1 and 2 for introducing aromatic reactant and alkylating reagent via introduction devices 24 and 30, respectively. Alternatively, fresh alkylating reagent feed can be directly introduced into the intermediate portions of either fluidized bed 14a or 14b, in the same manner as described above in conjunction with FIG. 1. The reactor product from vessel 12b is recovered as reactor outlet stream 40.

If desired, although not shown in the illustrated embodiment, at least a portion of the material withdrawn from reactor 12a can be passed through a product recovery system to separate the desired products from the reactants. This product recovery system can be the same as those described above.

As described above in conjunction with FIG. 2, the system 10 of FIG. 3 can use different fluidized and catalyst bed compositions, if necessary or desired, to optimize conversion, yield, and selectivity. Also, the various reactant charge rates can be separately controlled to optimize alkylated aromatic production.

Of course, more than two reactor vessels could be arranged in series, in the same manner shown in FIG. 3, without departing from the invention. In theory, any number of series connected reactors could be used. One potential drawback to such a system, including the system 10 illustrated in FIG. 3, includes its use of separate reactor vessels 12a and 12b and separate cyclones 22a and 22b for maintaining the separate fluidized beds. The use of separate equipment, while making it easy to maintain separate fluidized beds, increases the equipment costs and physical space associated with the system 10.

Additionally, if desired, either or both reactor vessels 12a and 12b may contain two or more discrete fluidized beds, like the reactor vessel 12 shown in FIG. 2.

The following examples are provided to more fully illustrate the invention and accent its advantageous features. These examples are included to illustrate the invention and should not be construed as limiting it in any way.

EXAMPLE 1

For this example, a reactor system like that illustrated in FIG. 1 was used, including a single reactor vessel and a single fluidized bed reaction zone. This fluidized bed pilot plant, used to produce xylene from toluene and methanol, was 10.2 cm (4 inches) in diameter and 8.2 m (27 feet) high. Methanol was introduced in a stagewise fashion, split between the various stages shown in the table that follows. At stage 1 (located at the bottom of the reactor), the methanol was pre-mixed with the toluene feed prior to introduction into the fluidized bed. Methanol introduction in each of the subsequent, downstream stages did not including pre-mixing with toluene. Rather, in these later stages, methanol was directly injected into the fluidized bed.

The fluidized bed catalyst used contained about 4 wt. % phosphorus and 10 wt. % of a 450/1 $SiO_2/Al_2O_3$ ZSM-5 zeolite in a binder comprising silica-alumina and clay. The catalyst was steamed at 14.7 psi partial pressure and 1000° C. for 45 minutes prior to use. It had a particle density of about 1.4 g/cc and a particle size range of 20 to 300 microns.

When running the pilot plant under the conditions described below, the following performance test results were obtained:

TABLE 1

| Number of Stages | 1 | 2 | 3 | 4 |
|---|---|---|---|---|
| Conditions | | | | |
| Reactor Top Pressure (psig) | 21 | 21 | 22 | 22 |
| Reactor Temperature (° F.) | 1105 | 1095 | 1104 | 1108 |
| Hydrocarbon WHSV (hr$^{-1}$) | 1.9 | 1.6 | 1.6 | 1.6 |

TABLE 1-continued

| Number of Stages | 1 | 2 | 3 | 4 |
|---|---|---|---|---|
| Methanol Overall WHSV (hr$^{-1}$) | 0.3 | 0.2 | 0.2 | 0.2 |
| % Methanol to Stage 1 (bottom) | 100 | 50 | 33 | 35 |
| % Methanol to Stage 2 | 0 | 50 | 33 | 26 |
| % Methanol to Stage 3 | 0 | 0 | 33 | 26 |
| % Methanol to Stage 4 | 0 | 0 | 0 | 13 |
| Stage 2 Elevation (feet) | — | 10.8 | 3.8 | 3.8 |
| Stage 3 Elevation (feet) | — | — | 10.8 | 10.8 |
| Stage 4 Elevation (feet) | — | — | — | 18.0 |
| Overall Molar Ratio of Toluene to Methanol | 2.0 | 2.0 | 2.0 | 2.0 |
| Water to Hydrocarbon Ratio | 0.5 | 0.5 | 0.5 | 0.5 |
| Reactor Inlet Velocity (ft/s) | 2.8 | 2.2 | 2.0 | 2.0 |
| Reactor Outlet Velocity (ft/s) | 3.2 | 3.1 | 3.0 | 3.0 |
| Average Reactor Bed Density (lb/ft$^3$) | 23 | 25 | 25 | 25 |
| Performance | | | | |
| Methanol Conversion (%) | 88.7 | 91.9 | 91.9 | 92.9 |
| Toluene Conversion (%) | 21.7 | 26.4 | 27.4 | 28.2 |
| Xylene Yield Based on Toluene (wt %) | 24.7 | 30.2 | 30.9 | 31.9 |
| Para-Xylene Selectivity (%) | 89.9 | 89.9 | 89.7 | 89.3 |
| Methanol Utilization (%) | 48.4 | 57.0 | 58.2 | 59.3 |

The above sample runs demonstrate the improved performance realized by the process and system according to the invention. Sample Run 1 was outside the scope of the present invention because it did not include introduction of the alkylating reagent (methanol) downstream from the location where the aromatic reactant (toluene) was introduced. Rather, in Sample Run 1, 100% of the methanol was introduced at the bottom of the fluidized bed, with the toluene feed. Sample Runs 2–4 were performed according to the system and process of this invention.

As the performance data demonstrates, the sample runs using the system and process according to the invention (Sample Runs 2–4) provided improved methanol and toluene conversion, improved xylene yield, and improved methanol utilization over Sample Run No. 1. All of these improved results were achieved with insignificant or no reduction in para-xylene selectivity.

EXAMPLE 2

This Example demonstrates that generally increasing the number of alkylation reagent introduction stages can improve the performance of the invention for toluene conversion and methanol utilization. The sample runs described below, both run according to the process of this invention, were performed on the pilot plant used in Example 1. The operating conditions and performance results are set forth in Table 2.

TABLE 2

| Number of stages | 2 | 4 |
|---|---|---|
| Conditions | | |
| Reactor Top Pressure (psig) | 20 | 20 |
| Reactor Temperature (° F.) | 1104 | 1102 |
| Hydrocarbon WHSV (hr$^{-1}$) | 1.5 | 1.5 |
| Methanol Overall WHSV (hr$^{-1}$) | 0.2 | 0.2 |
| % Methanol to Stage 1 (bottom) | 49 | 27 |
| % Methanol to Stage 2 | 51 | 24 |
| % Methanol to Stage 3 | 0 | 24 |
| % Methanol to Stage 4 | 0 | 25 |
| Stage 2 Elevation (feet) | 10.8 | 3.8 |
| Stage 3 Elevation (feet) | — | 10.8 |
| Stage 4 Elevation (feet) | — | 18.0 |
| Overall Molar Ratio of Toluene to Methanol | 1.8 | 1.8 |
| Water to Hydrocarbon Ratio | 0.5 | 0.5 |
| Reactor Inlet Velocity (ft/s) | 2.1 | 1.9 |
| Reactor Outlet Velocity (ft/s) | 3.1 | 3.2 |
| Average Reactor Bed Density (lb/ft$^3$) | 27 | 27 |
| Performance | | |
| Methanol Conversion (%) | 99.3 | 97.9 |
| Toluene Conversion (%) | 33.2 | 35.4 |
| Xylene Yield Based on Toluene (wt %) | 37.3 | 38.7 |
| Para-Xylene Selectivity (%) | 88.7 | 89.7 |
| Methanol Utilization (%) | 58.8 | 61.8 |

As evident from this performance data, both processes according to the invention produced excellent results. When increasing the number of methanol introduction stages from two to four, however, increases in toluene conversion and methanol utilization were realized. This data parallels that shown in Example 1. Additionally, the four stage introduction process showed improvement in xylene yield and para-xylene selectivity.

While the invention has been described herein in terms of various preferred embodiments, those skilled in the art will recognize that various changes and modifications can be made without departing from the spirit and scope of the invention, as defined in the following claims.

What is claimed is:

1. A process for alkylating an aromatic hydrocarbon reactant with an alkylating reagent comprising methanol to produce an alkylated aromatic product, comprising:

introducing the aromatic hydrocarbon reactant into a reactor system at a first location, wherein the reactor system includes a fluidized bed reaction zone comprising a temperature of 500° to 700° C. and an operating bed density of about 300 to 600 kg/m$^3$, for producing the alkylated aromatic product;

introducing a plurality of streams of said alkylating reactant directly into said fluidized bed reaction zone at positions spaced apart in the direction of flow of the aromatic hydrocarbon reactant, at least one of said streams being introduced at a second location downstream from the first location; and recovering the alkylate aromatic product, produced by reaction of the aromatic reactant and the alkylating reagent, from the reactor system.

2. A process according to claim 1, wherein said fluidized bed reaction zone includes a top portion, a bottom portion, and an intermediate portion extending between the top portion and the bottom portion, wherein the first location where the aromatic hydrocarbon reactant is introduced is provided at or near the bottom portion of the fluidized bed reaction zone, and the second location where said at least one stream of the alkylating reagent is introduced is provided in the intermediate portion of said fluidized bed reaction zone.

3. A process according to claim 2, wherein a plurality of streams of the alkylating reagent are introduced directly into the intermediate portion of the fluidized bed reaction zone at a plurality of different axial positions in the intermediate portion of the fluidized bed reaction zone.

4. A process according to claim 2, wherein the fluidized bed reaction zone is a dense fluid bed, and a plurality of streams of the alkylating reagent are introduced directly into the intermediate portion of the fluidized bed reaction zone at a plurality of different axial positions in the intermediate portion of the fluidized bed reaction zone.

5. A process according to claim 1, wherein the aromatic hydrocarbon reactant includes toluene, the alkylating reagent includes methanol, and the alkylated aromatic product includes xylene.

6. A process according to claim 1, further including introducing a stream of alkylating reagent at the first location where the aromatic hydrocarbon reactant is introduced into the reactor system.

7. A process according to claim 6, wherein the additional alkylating reagent is introduced in a common feed stream with the aromatic hydrocarbon reactant.

8. The process of claim 1 which comprises an operating bed density of 300 to 500 kg/m$^3$, pressures of 1 atmosphere to 1000 psig, a weight hourly space velocity for total hydrocarbon feed to the reactor(s) of 0.2 to 1000 for the aromatic reactant, and about 0.01 to 100 for the combined alkylating reagent stage flows, based on total catalyst in the reactor(s).

9. The process of claim 8 wherein said aromatic reactant comprises toluene and said alkylating reagent comprises methanol, and which further comprises moles toluene/moles methanol (in the reactor charge) of at least about 0.2.

10. The process of claim 9 which is conducted in the presence of added hydrogen and/or added water such that the molar ratio of hydrogen and/or water to toluene+methanol in the feed to the reactor is between 0.01 and 10.

11. The process of claim 8 which comprises temperatures of 500° to 600° C., pressures of 10 psig to 200 psig, a weight hourly space velocity of 0.5 to 500 for the aromatic reactant, and 0.01 to 100 for the combined alkylating reagent stage flows, based on total catalyst in the reactor(s).

12. The process of claim 11 which further comprises moles toluene/moles methanol (in the reactor charge) of 0.2 to 20.

13. The process of claim 1 wherein said reactor system contains a ZSM-5 zeolite alkylation catalyst.

14. The process of claim 1 wherein said reactor system contains a selectivated catalyst.

15. The process of claim 9 wherein said reactor system contains 50/1 SiO$_2$/Al$_2$O$_3$ ZSM-5 zeolite in a binder comprising silica-alumina and clay.

16. The process of claim 1 wherein said fluidized bed reaction zone is operated at a temperature of 590° to 700° C.

17. A process for alkylating an aromatic hydrocarbon reactant with an alkylating reagent comprising methanol to produce an alkylated aromatic product, comprising:

introducing the aromatic hydrocarbon reactant into a reactor system at a first location, wherein the reactor system includes a fluidized bed reaction zone comprising a temperature of 500° to 700° C. and an operating bed density of about 300 to 600 kg/m$^3$, for producing the alkylated aromatic product and wherein the fluidized bed reaction zone has a substantially uniform cross-section;

introducing a plurality of streams of said alkylating reactant directly into said fluidized bed reaction zone at positions spaced apart in the direction of flow of the aromatic hydrocarbon reactant, at least one of said streams being introduced at a second location downstream from the first location; and recovering the alkylate aromatic product, produced by reaction of the aromatic reactant and the alkylating reagent, from the reactor system.

* * * * *